United States Patent [19]

Voda

[11] Patent Number: 5,401,258
[45] Date of Patent: Mar. 28, 1995

[54] CORONARY GUIDE CATHETER

[76] Inventor: Jan Voda, 1404 Camden Way, Oklahoma City, Okla. 73116

[21] Appl. No.: 246,552

[22] Filed: May 19, 1994

Related U.S. Application Data

[63] Continuation of Ser. No. 988,355, Dec. 9, 1992, abandoned, which is a continuation of Ser. No. 622,873, Jan. 23, 1991, abandoned.

[51] Int. Cl.$^6$ ............................................. A61M 25/14
[52] U.S. Cl. ........................................ 604/281; 604/280
[58] Field of Search ................. 604/264, 280, 281, 96; 128/656-658; 606/108, 194

[56] References Cited

U.S. PATENT DOCUMENTS

| | | | |
|---|---|---|---|
| 3,935,857 | 2/1976 | Co | 128/658 |
| 3,938,501 | 2/1976 | Erikson | 128/658 |
| 4,020,829 | 5/1977 | Willson et al. | 128/657 |
| 4,033,331 | 7/1977 | Guss et al. | 128/657 |
| 4,117,836 | 10/1978 | Erikson | 128/658 |
| 4,169,464 | 10/1979 | Obrez | 128/657 |
| 4,195,637 | 4/1980 | Gruntzig et al. | 128/348 |
| 4,292,976 | 10/1981 | Banka | 128/656 |
| 4,430,083 | 2/1984 | Ganz et al. | 604/283 |
| 4,547,193 | 10/1985 | Rydell | 128/658 |
| 4,551,292 | 11/1985 | Fletcher et al. | 128/658 |
| 4,563,181 | 1/1986 | Wijayarathna et al. | 128/656 |
| 4,568,338 | 2/1986 | Todd | 604/281 |
| 4,733,669 | 3/1988 | Segal | 128/663 |
| 4,738,667 | 4/1988 | Galloway . | |
| 4,747,840 | 5/1988 | Lakika et al. | 604/280 |
| 4,781,682 | 11/1988 | Patel | 604/280 |
| 4,784,639 | 11/1988 | Patel | 128/658 |
| 4,790,831 | 12/1988 | Skribiski | 604/282 |
| 4,813,930 | 3/1989 | Elliott | 604/53 |
| 4,820,349 | 4/1989 | Saab | 128/344 |
| 4,822,345 | 4/1989 | Danforth | 604/282 |
| 4,867,174 | 9/1989 | Skribiski | 128/657 |
| 4,882,777 | 11/1989 | Narula | 604/281 |
| 4,883,058 | 11/1989 | Ruiz | 128/654 |
| 4,886,506 | 12/1989 | Lovgren et al. | 604/282 |
| 4,898,577 | 2/1990 | Badger et al. . | |
| 4,898,591 | 2/1990 | Jang et al. | 604/282 |
| 4,909,787 | 3/1990 | Danforth | 604/95 |
| 4,925,445 | 5/1990 | Sakamoto et al. . | |
| 4,935,004 | 6/1990 | Cruz . | |
| 4,935,017 | 6/1990 | Sylvanowicz . | |
| 4,950,228 | 8/1990 | Knapp, Jr. et al. . | |
| 4,976,691 | 12/1990 | Sahota | 128/772 |
| 4,981,477 | 1/1991 | Schon et al. | 604/281 |
| 4,983,166 | 1/1991 | Yamawaki | 604/281 |
| 4,994,032 | 2/1991 | Sugiyama et al. | 604/96 |
| 5,000,743 | 3/1991 | Patel | 606/194 |
| 5,044,369 | 9/1991 | Sahota | 128/658 |
| 5,045,072 | 9/1991 | Castillo et al. | 128/658 |
| 5,058,595 | 10/1991 | Kern | 604/281 |
| 5,059,197 | 10/1991 | Urie et al. | 128/657 |
| 5,098,412 | 3/1992 | Shiu | 604/280 |
| 5,122,125 | 6/1992 | Deuss | 604/280 |
| 5,163,921 | 11/1992 | Feiring | 604/247 |
| 5,195,990 | 3/1993 | Weldon . | |
| 5,203,776 | 4/1993 | Durfee | 604/264 |

OTHER PUBLICATIONS

Mallinckrodt "Diagnostic Catheters" Brochure 1990.
Bourassa "Cardiovascular Catheters Sterile" Brochure, Jun. 1972.
USCI "KIFA Products" Brochure pp. 1-12 Jun. 1974.
USCI KIFA Products "Catheterization Equipment" Brochure pp. 1-7 1967.
*U.S.C.I. Gruntzig Dilaca Coronary Dilatation Equipment*, U.S.C.I., C. R. Bard, Inc. 1990.
U.S.C.I. "Positrol II and Nycore ™ Cardiovascular Catheter".

(List continued on next page.)

*Primary Examiner*—C. Fred Rosenbaum
*Assistant Examiner*—Mark Bockelman
*Attorney, Agent, or Firm*—Nawrocki, Rooney & Sivertson

[57] ABSTRACT

A catheter for insertion into an artery of a cardiovascular system including a first straight portion extending from the proximal end of the catheter for a distance greater than the length of the artery and a distal end portion extending from the straight portion and bent in a unique manner to enable the distal end to be precisely located relative to the artery.

6 Claims, 6 Drawing Sheets

OTHER PUBLICATIONS

Arani STE: *A new catheter for angioplasty of the right coronary artery and aorta coronary bypass grafts,* Cath. Cardiovasc. Diag. 11:647–658, 1985.

Block, P. C. et al.: *PTCA in perspective,* U.S.C.I. Division, C. R. Bard, Inc. Billerica, Mass., pp. 23–41 1986.

King, S. B., III and Douglas S. Jr.: *Coronary Arteriography and Angioplasty,* McGraw-Hill, New York, Chapter 17, *Percutaneous Transluminal Coronary Angioplasty,* pp. 433–452, 1985.

Amplatz, K. et al., *Mechanics of Selective Coronary Artery Catheterization via Femoral Approach,* Radiology 89: 1040–1047, Jul. 1967.

Judkins, M., *Percutaneous Transfemoral Selective Coronary Arteriography,* Radiologic Clinics of North America—vol. VI, No. 3, Dec. 1968.

Carr, M., *The Use of the Guiding Catheter in Coronary Angioplasty: The Technique of Manipulating Catheters to Obtain the Necessary Power to Cross Tight Coronary Stenoses,* Catheterization and Cardiovascular Diagnosis 12: 189–197 (1986).

"Angled Tip of the Steerable Guidwire and Its Usefulness in Percutaneous Transluminal Coronary Angioplasty", Jan Voda, *Use of Angled Guidewires in PTCA,* 1987, pp. 204–210.

USCI Video Tape: *Select Curve Guiding Catheters: Cannulating the Right Coronary Artery,* USCI, C. R. Bard, 1988. See Transcript on IDS May 19, 1994.

USCI Block TM Right Coronary Guiding Catheter, 1989, 2 pages.

USCI Video Tape ("Select Curve Guiding Catheter: Cannulating the Right Coronary Artery") transcript and selected figures, 1988.

"Coronary Arteriography and Angioplasty" Spencer B. King III, John S. Douglas pp. 182–238.

Medi-Tech—Boston Scientific Corporation "Imager Angiographic Catheters" Brochure Oct. 1990.

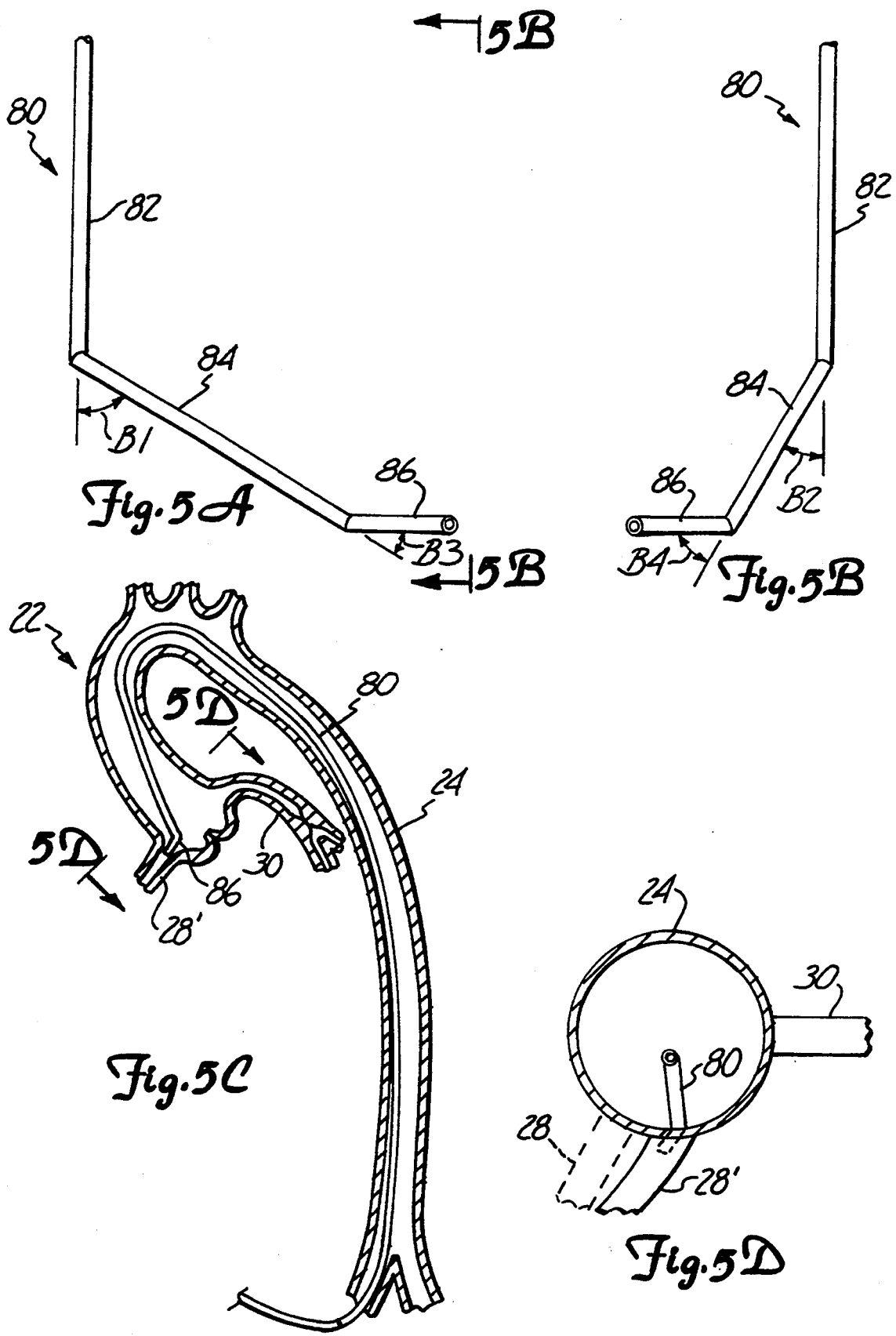

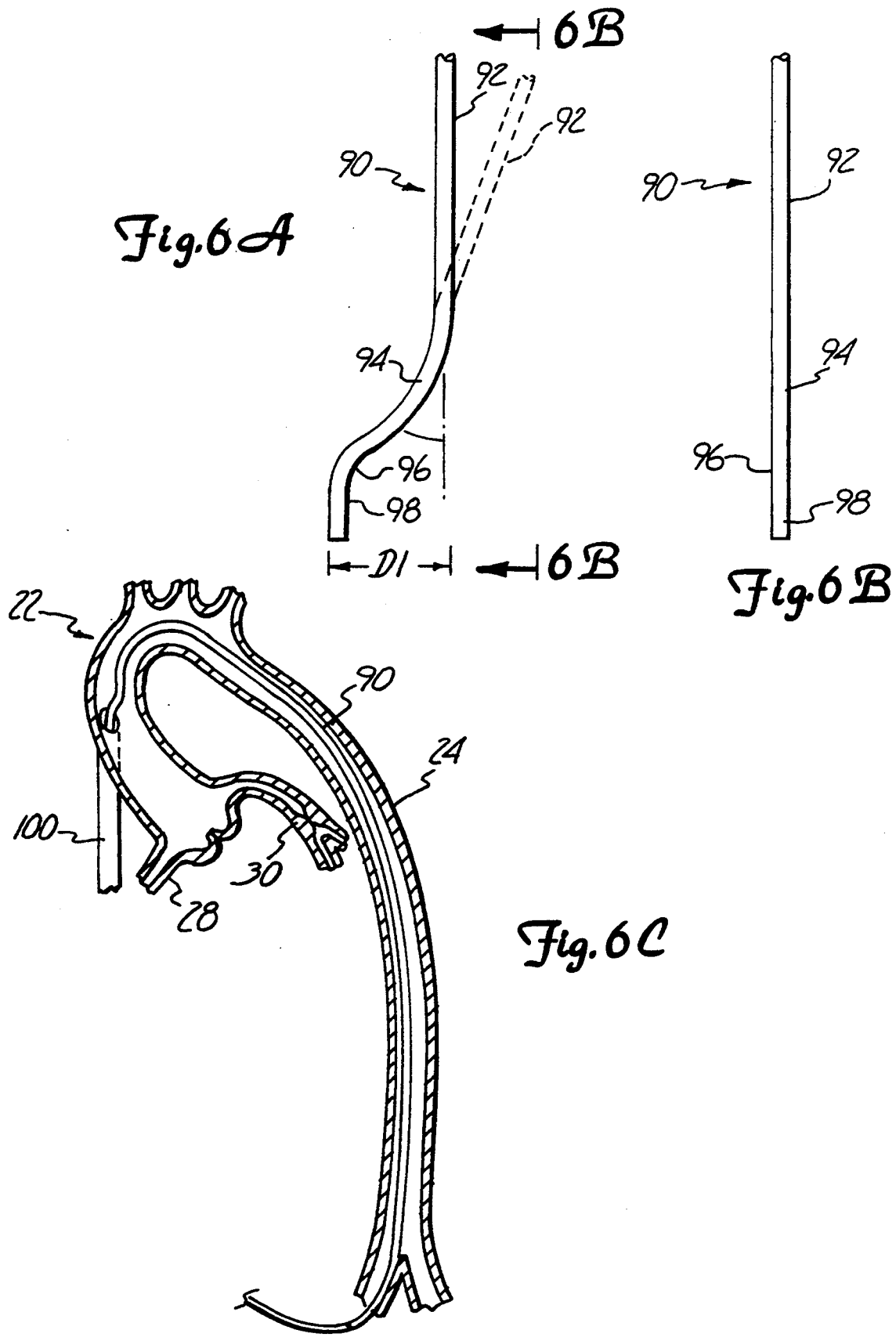

CORONARY GUIDE CATHETER

This is a continuation of application(s) Ser. No. 07/988,355, filed on Dec. 9, 1992, abandoned, which is a continuation of application Ser. No. 07/662,873, filed on Jan. 23, 1991, now abandoned.

BACKGROUND OF THE INVENTION

This invention relates generally to catheters adapted to be inserted into the cardiovascular system of a living body and, more particularly, to an improved catheter having an improved distal end portion for more precise location in the particular artery of the cardiovascular system.

Catheters are often used in the performance of medical procedures such as coronary angiography for injecting dye, or the like, into the cardiovascular system for diagnosis; and angioplasty to widen the lumen of a coronary artery which has become at least partially blocked by a stenotic lesion causing an abnormal narrowing of the artery due to injury or disease. In these techniques the distal end of the catheter is introduced into the aorta by way of the femoral artery. The proximal end of the catheter is then manipulated so its distal end is inserted into the lumen of a selected coronary artery branching off from the aorta. A typical angioplasty procedure would involve initially inserting a guiding catheter into the cardiovascular system in the above manner, followed by a dilating catheter, a laser catheter, an atherectomy catheter, or the like, which is guided through the guiding catheter until its distal end portion is positioned within the stenotic lesion in the coronary artery to reduce the blockage in the artery. A diagnostic catheter would be used in the same manner.

The most common catheter used in treatment of the left coronary artery is what is often referred to as a "Judkins" catheter which has a specially shaped distal end portion for facilitating insertion into the artery. However, as will be specifically discussed, there are some disadvantages to the "Judkins" catheter, including its inability to align perfectly coaxially with selected artery and thus permit optimum treatment, and its inability to adequately support other devices such as balloon catheters. Also, the Judkins catheter forms relatively large angles when inserted into the cardiovascular system thus dissipating some of the axial forces transmitted through the catheter during use.

SUMMARY OF THE INVENTION

It is therefore an object of the present invention to provide a catheter of the above type which enables precise location of the distal end portion of the catheter relative to the desired coronary artery to be treated.

It is a further object of the present invention to provide a catheter of the above type which is easy to manipulate and which enables the distal end portion to be precisely aligned coaxially in the coronary artery to be treated.

It is a further object to provide a guiding catheter of the above type which provides increased support for balloon catheters and other similar devices.

It is a further object of the present invention to provide a catheter of the above type which minimizes the dissipation of axial forces through the catheter during use.

Toward the fulfillment of these and other objects, the catheter of the present invention includes a first straight portion extending from the proximal end of the catheter for a distance greater than the length of the artery and a distal end portion extending from the straight portion and bent in a unique manner to enable the distal end to be precisely located relative to the artery.

DESCRIPTION OF THE DRAWINGS

The above brief description, as well as further objects, features and advantages of the present invention will be more fully appreciated by reference to the following detailed description of the presently preferred but nonetheless illustrative embodiments in accordance with the present invention when taken in conjunction with the accompanying drawings wherein:

FIGS. 2A-2C, 3A-3C, and 6A-6C are views similar to FIGS. 1A-1C, respectively, but depicting alternate embodiments of the present invention; and FIGS. 4A-4D and FIGS. 5A-5D are views similar to 1A-1D, respectively, but depicting additional three embodiments of the catheter of the present invention.

DESCRIPTION OF THE PRIOR ART

Figure 1A:
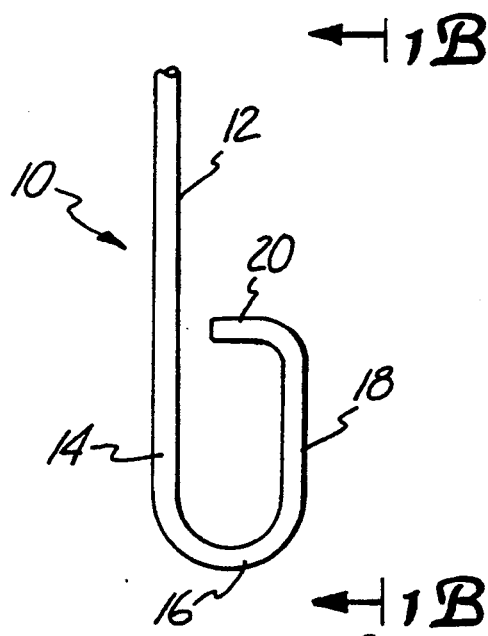
FIGS. 1A and 1B are side and front views, respectively, of a portion of the catheter of the prior art.
Figure 1B:
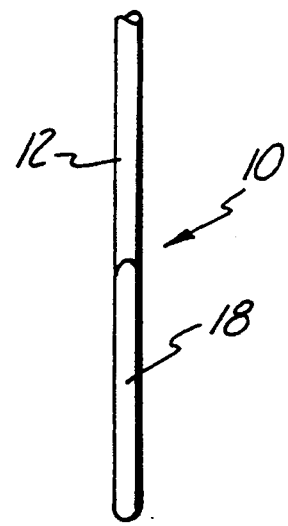

Referring to FIGS. 1A and 1B of the drawings, the reference numerical 10 refers, in general, to a well known prior art catheter, commonly referred to as a "Judkins" catheter. The catheter 10 is in the form of an elongated tubular member having a straight portion 12 (shown partially in FIGS. 1A and 1B) and a distal end portion consisting of a straight portion 14 forming an extension of the straight portion 12. The tubular member is bent to form a curved portion 16 which extends from the straight portion 14 for approximately 180 degrees. A straight portion 18 extends from the curved portion 16 and parallel to the straight portion 14. A tip portion 20 extends from, and is perpendicular to, the straight portion 18. A typical Judkins catheter would have straight portions 18 and 20 of 4 centimeters ("cm.") and 1 cm., respectively, in length; and the curved portion 16 would have a radius of curvature of approximately 1 cm. The catheter 10 is usually fabricated of a plastic material selected to exhibit flexibility and softness yet permit adequate "torque control" i.e., the ability to transmit twisting forces along its length so that it can be located and maneuvered precisely within a cardiovascular system by skilled manipulation of its proximal end, as will be described.

Figure 1C:
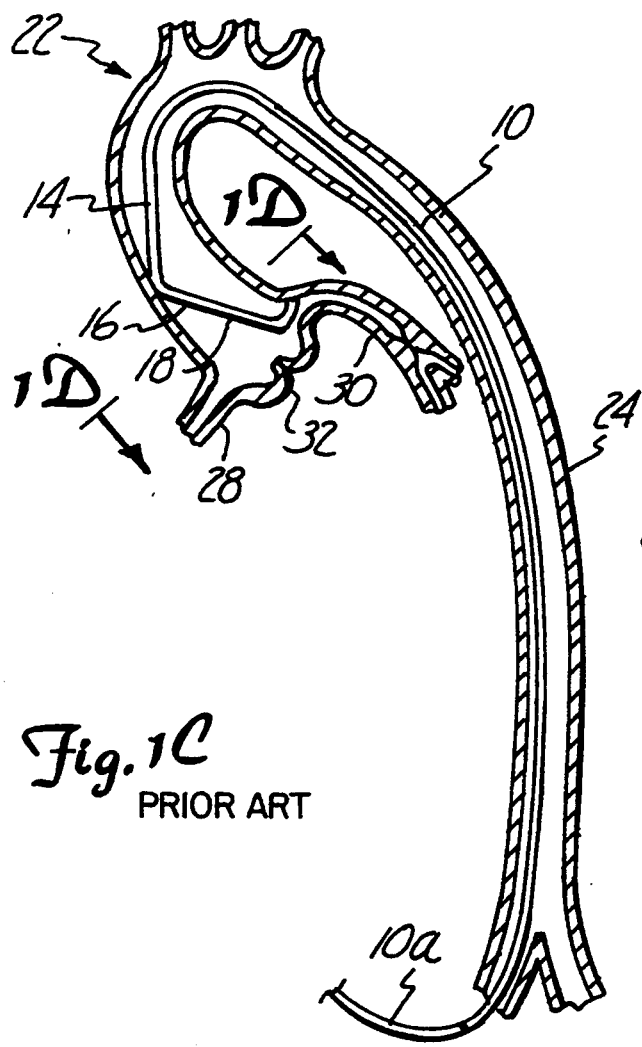
FIG. 1C is a cross sectional view of a portion of a cardiovascular system with the catheter of FIGS. 1A and 1B inserted therein.
Figure 1D:
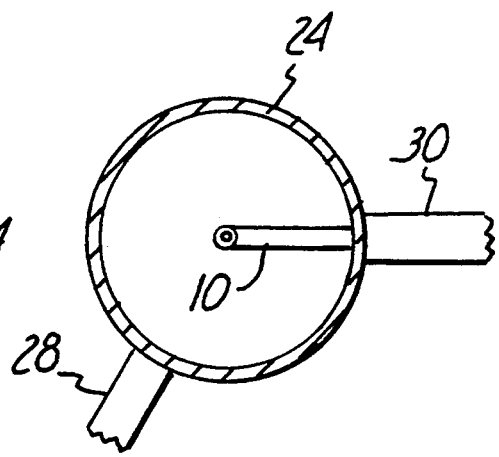
FIG. 1D is an enlarged cross-sectional view taken along the line 1D—1D FIG. 1C.

A typical cardiovascular system is shown in FIGS. 1C and 1D and is referred to, in general, by the reference numeral 22. The system 22 includes an aorta 24 which extends through the body and curves around for approximately 180 degrees and then branches into a right coronary artery 28 and a left main coronary artery 30. An aortic valve 32 extends between the right coronary artery 28 and the left main coronary artery 30 and is connected to the heart (not shown). As better shown in FIG. 1D, the right coronary artery 28 and the left main coronary artery 30 are normally angularly spaced approximately 120 degrees.

The prior art catheter 10 is designed for use as a diagnostic catheter or a guiding catheter for treatment of stenotic lesions, or the like, in the left coronary artery 30. To this end, the catheter 10 is inserted into the system 22 and is manipulated so that, ideally, the leading, or distal, end portion of the catheter 10 is positioned into the lumen of, the left main coronary artery 30 and used to guide other catheters, such as balloon, laser or atherectomy catheters, or the like (not shown) into the left main coronary artery 30.

To assist in advancing the catheter 10 through the system 22 a relatively stiff wire is initially inserted into the catheter 10 to straighten it out and, after the catheter is completely inserted, the wire is withdrawn, causing the catheter to take the position shown in FIG. 1C. During this procedure, the proximal end portion 10a of the catheter extends outside the system 22 and is manipulated by rotation and guidance in a known manner until the tip portion 20 hopefully aligns with the left main coronary artery 30 in a coaxial relationship. As a result of this operation, the straight portions 14 and 18 are spread apart and the end of the tip portion 20 is inserted in the lumen of the left main coronary artery 30.

However, due to the particular configuration of the Judkins catheter 10, the tip 20 is often misaligned with the left main coronary artery 30 as shown in FIG. 1C, and is thus not located coaxially with the latter artery. Thus, when an inner catheter (not shown) is passed through the catheter 10, the former often strikes the wall of the aorta or left main coronary artery increasing the risk of damage. Also, the catheter 10 does not provide optimum support and guidance of other catheters or devices that are passed through the catheter 10. Further, the curved position 16, which is shown resting against the inner wall of the aorta 24 in FIG. 1C, is located a considerable distance above the ostuim of the artery 30, thus dissipating some of the axial forces transmitted through the catheter during manipulation thereof.

DESCRIPTION OF THE PREFERRED EMBODIMENT

Figures 2A, 2B:
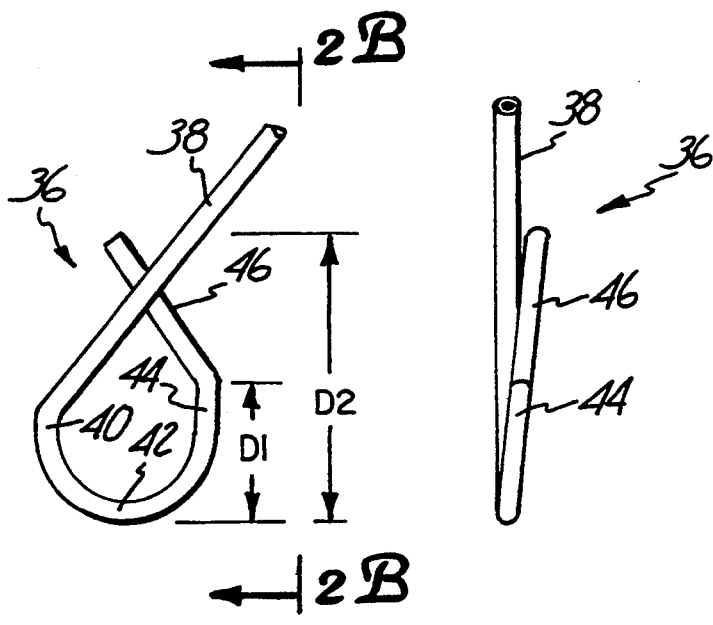

The catheter of the present invention is specifically designed to overcome the aforementioned deficiencies of the Judkins type catheter 10, and one embodiment of the catheter of the present invention is shown in general by the reference numeral 36 in FIGS. 2A and 2B. The catheter 36 is in the form of an elongated tubular member having a straight portion 38 (shown partially in FIGS. 2A and 2B) and extending from the proximal end portion (not shown) of the catheter. The catheter 36 includes a distal end portion formed by a straight portion 40, a curved portion 42, another straight portion 44 and a tip portion 46. The straight portion 40 extends at an angle to the straight portion 38, and the curved portion 42 extends from the straight portion 40 for approximately 180 degrees. The straight portion 44 extends from the curved portion 42 and parallel to the straight portion 40, and the tip portion 46 extends from, and at an angle to, the straight portion 44. According to a feature of the embodiment of FIGS. 2A and 2B, the distance D1 (measured vertically as viewed in FIGS. 2A and 2B) between the outer curvature of the curved portion 42 and the junction between the straight portion 44 and 46 is one-half the distance D2 between the latter outer curvature and the end of the tip portion 46.

For example, the distance between the outer curvature of the curved portion 42 and the junction of the straight portion 40 and the straight portion 38 is approximately 1.5 cm., the distance D1 is approximately 2 cm. and the distance D2 is approximately 4 cm. The radius of the curved portion 42 is approximately 1 cm. which forms a diameter of 2 cm. corresponding to the distance between the straight portions 40 and 44. The angle between the straight portions 38 and 40 is between 30 degrees and 50 degrees, and the angle between the straight portions 44 and 46 is between 20 degrees and 50 degrees. It is understood that these distances and angles represent only one possible configuration of the catheter 36. For example, the length of straight portion 40 can be increased to other values within the scope of the invention and thus provide increased support.

The catheter 36 can be fabricated of a material, such as plastic, which exhibits optimum flexibility and softness while permitting the transmission of twisting forces along its length by manipulation of its proximal end.

Figure 2C:
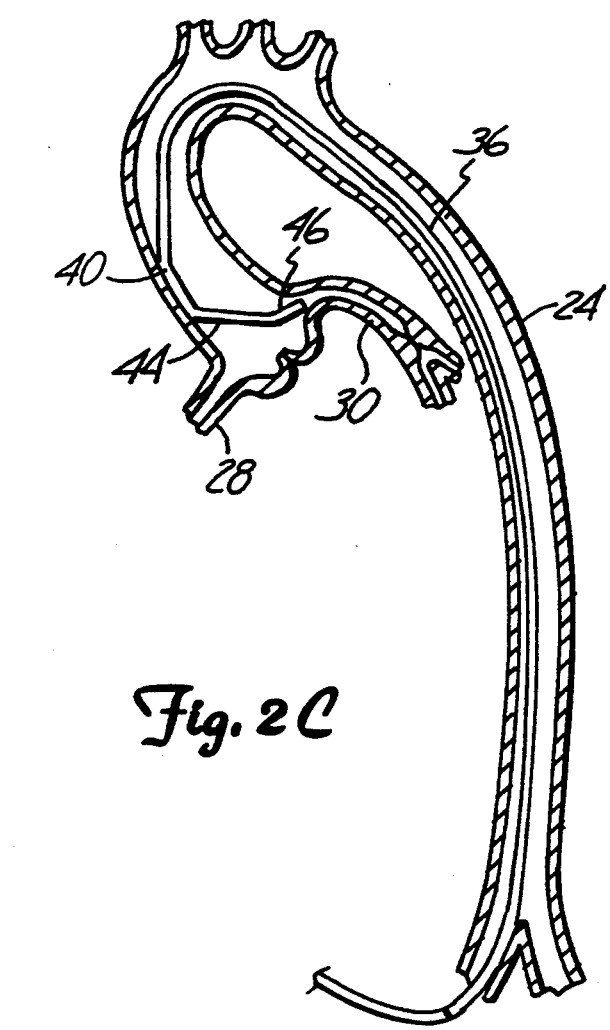

FIG. 2C depicts the cardiovascular system 22 of FIG. 1C with the catheter 36 inserted therein. Prior to insertion a relatively stiff wire (not shown) is inserted in the catheter 36 and the catheter inserted in the system 22. Then the wire is withdrawn and the catheter 36, by virtue of its pre-shape shown in FIGS. 2A and 2B, takes the position shown with the tip portion 46 precisely aligned with the lumen of the left main coronary artery 30 in a coaxial relationship. It is also noted that, as a result of the foregoing, a greater portion of the catheter 36 rests against the inner wall of the aorta 24 and bends at a lesser angle when compared to the Judkins catheter 10. Also the straight portion 40 rests against the inner wall of the aorta 24 and is lower in the artery, and thus more opposite the ostium of the artery 30, when compared to the Judkins catheter 10. Thus, the axial forces transmitted along the length of the catheter 36 are better transmitted to the end portion thereof for more precise manipulation and location.

Figures 3A, 3B:
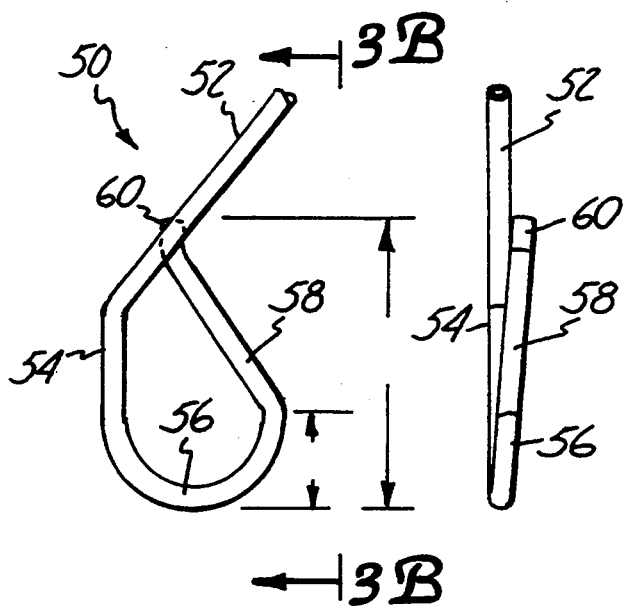

An alternate embodiment of the catheter of the present invention is shown in general by the reference numeral 50 in FIGS. 3A and 3B. The catheter 50 is in the form of an elongated tubular member having a straight portion 52 (shown partially in FIGS. 3A and 3B) and a distal end portion consisting of a straight portion 54, a curved portion 56, a straight portion 58, and a tip portion 60. The straight portion 54 extends at an angle to the straight portion 52, and the curved portion 56 extends from the straight portion 54 for approximately 180 degrees. The straight portion 58 extends from the curved portion 56 at an angle to the straight portion 54. The tip portion 60 extends at an angle to the straight portion 58 and parallel to the straight portion 54. The end of the tip portion 60, which forms the distal end of the catheter 50, extends behind the straight portion 52 as viewed in FIG. 3A.

According to a feature of this embodiment, the distance D1, measured vertically as viewed in FIGS. 3A and 3B, between the outer curvature of the curved portion 56 and the junction between the straight portion 58 and the curved portion 56 is approximately one-third the distance between the latter curvature and the end of the tip portion 60.

For example, the distance between the outer curvature of the curved portion 56 and the junction of the straight portion 52 and the straight portion 54 could be approximately 3.0 cm., the length of the tip portion 60 is approximately 0.5 cm., the distance D1 is approximately 1.3 cm. and the distance D2 is approximately 4.0 cm. The angle that the straight portion 52 makes with the straight portion 54 is between 30 degrees and 50 degrees, and the angle that the straight portion 58 makes with the straight portion 54 is 20–40 degrees.

Figure 3C:
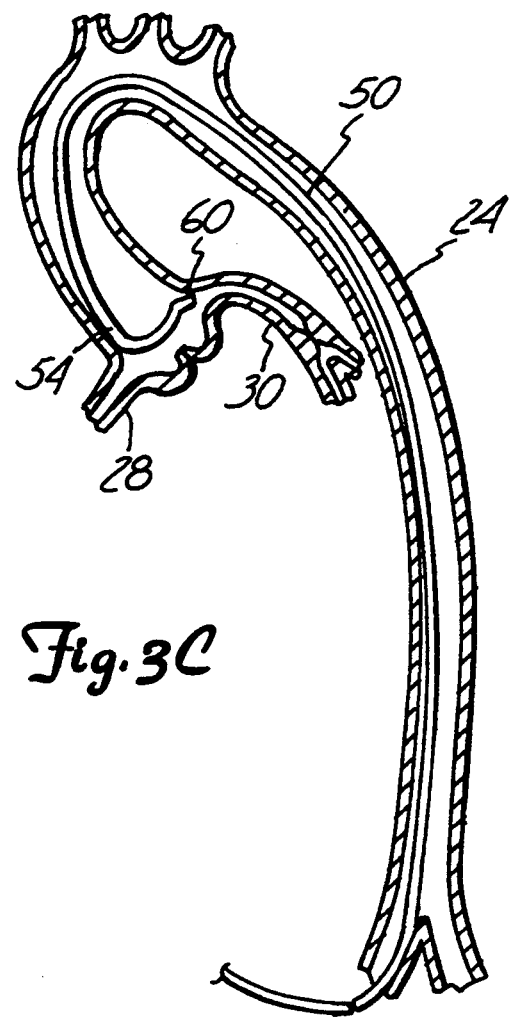

Referring to FIG. 3C, the catheter 50 is inserted in the cardiovascular system 22 in the manner described above. Due to the pre-shape of the catheter 50 shown in FIGS. 3A and 3B, the tip portion 60 is substantially coaxially aligned with the lumen of the left main coronary artery 30 and a portion of the catheter 50 lies in contact with the inner wall of the aorta 24. Thus the embodiment FIGS. 3A–3C enjoys the advantages of the embodiment of FIGS. 2A–2C.

Figure 4A:
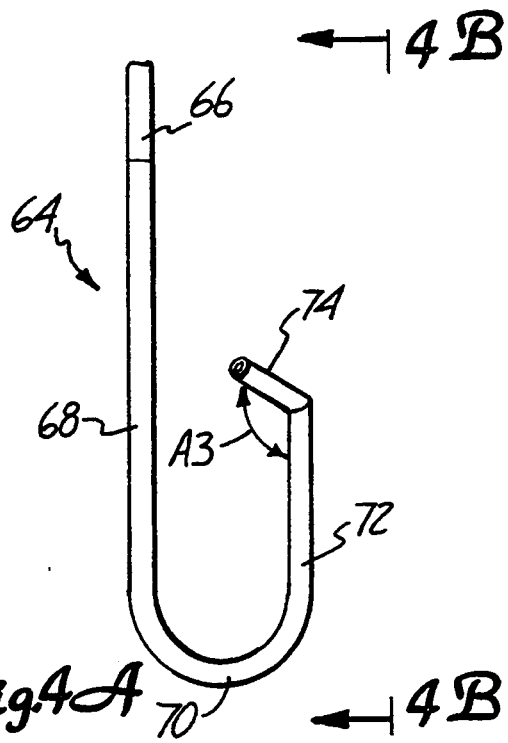
Figure 4B:
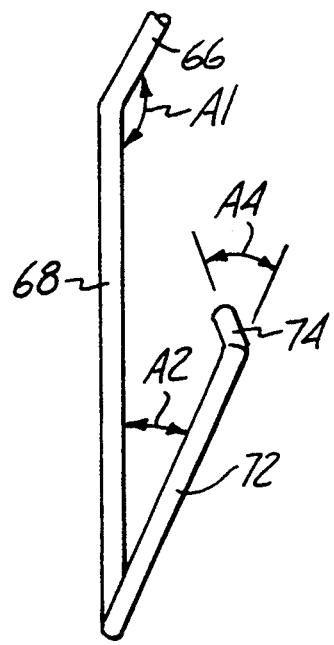

The catheter depicted in the alternate embodiment of FIGS. 4A and 4B is shown in general by the reference numeral 64, and is for a special application commonly referred to as "posterior take-off" of the left main coronary artery, as will be described. The catheter 64 is in the form of an elongated tubular member having a straight portion 66 (shown partially in FIGS. 1A and 1B) extending from the proximal end of the catheter, and a distal end portion consisting of a straight portion 68 a curved portion 70, a straight portion 72 and a tip portion 74. The straight portion 68 extends at an angle to the straight portion 66, and the curved portion 70 extends from the straight portion 68 for approximately 180 degrees. The straight portion 72 extends from the curved portion 70, and the tip portion 74 extends from, and at an angle to the straight portion 72.

As better shown in FIG. 4B, the straight portions 66 and 72 are bent out of the plane formed by the straight portion 68 and the curved portion 70. The straight portion 66 extends at an angle A1 of between 60 degrees and 70 degrees, to the straight portion 68 and the straight portion 72 extends at an angle A2 of between 20 degrees and 40 degrees to the straight portion 68. The length of the portions 68, 72 and 74 are approximately 6 cm., 3 cm. and 1.5 cm., respectively and the radius of the curved portion 70 is approximately 1 cm. The tip portion 74 extends at an angle A3 of between 40 degrees and 50 degrees from the straight portion 72 in a first plane (FIG. 4A), and at an angle A4 from the straight portion 72 (FIG. 4B) of between 25 degrees and 35 degrees in a second plane perpendicular to the first plane.

Figure 4C:
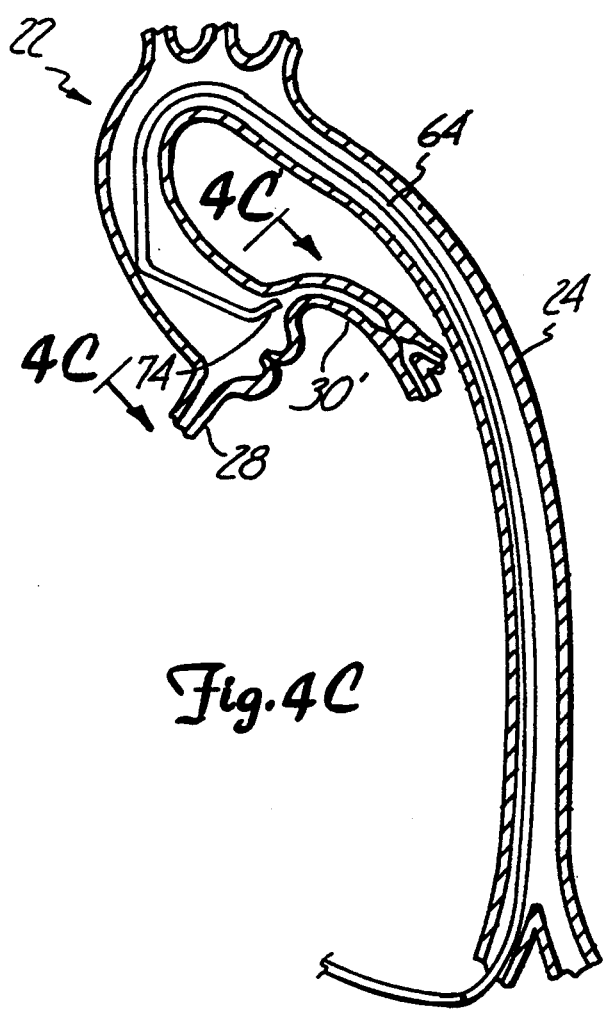
Figure 4D:
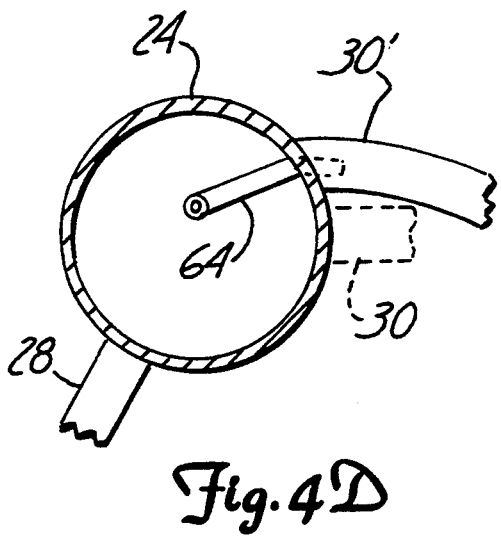

The catheter 64 has a special application in connection with a cardiovascular system 22 in which the left main coronary artery 30 is angularly displaced posteriorly a finite distance from its normal location as shown in FIG. 4D. More particularly, the normal position of the left main coronary artery is shown by the dashed lines and by the reference numeral 30. However the left main coronary artery sometimes is angularly displaced posteriorally from its normal position to a position shown, for example, by the solid lines and by the reference numeral 30'. The catheter 64 is especially configured for this location and, when inserted into the cardiovascular system 22 in the manner described above, it takes the position shown in FIG. 4C, with the angled tip 74 coaxially aligned with the lumen of the left maid coronary artery 30' notwithstanding the posterior displacement of the artery. The principles of the long tip catheter can also be applied to this catheter 64, particularly adding a 1.5 to 3.0 cm. long segment proximally for better support and extending the tip of the catheter to 2.0 or 2.5 cm.

Another embodiment of the catheter of the present invention is shown in general by the reference numeral 80 in FIGS. 5A and 5B and is also a special application catheter designed for treatment of a right coronary artery that is angularly displaced from its normal position and has an anterior takeoff. More particularly, the catheter 80 consists of a elongated tubular member having a straight portion 82 (shown partially in FIGS. 5A and 5B) and a distal end portion formed by a straight portion 84 and a tip portion 86. The straight portion 84 extends from the straight portion 82 at an angle B1 in a first plane (FIG. 5A) which is between 50 degrees and 70 degrees, and, as shown in FIG. 5B, at an angle B2 in a second plane perpendicular to the first plane which is between 20 degrees and 40 degrees. The tip portion 86 extends from the straight portion 84 and is also angled with respect thereto in two planes. Referring to FIG. 5A, the tip portion 86 extends from the straight portion 84 at an angle B3, which may be between 20 and 30 degrees, in the first plane. As shown in FIG. 5B, the tip portion 86 extends at an angle B4 of between 40 degrees and 50 degrees to the straight portion 84. The length of the straight portions 84 and 86 can be 6 cm. and 1.5–2.0 cm., respectively.

As shown in FIGS. 5C and 5D, the catheter 80 is designed for treatment of a right coronary artery 28' (FIG. 5D) which is shown anteriorly displaced from its normal position shown by the reference numeral 28. As a result of the preshape of the catheter 80 shown in FIGS. 5A and 5B, after insertion in the cardiovascular system 22 in the manner described above, it takes the position shown in FIG. 5C with the angled tip portion 86 extending in more coaxial alignment with the lumen of the displaced right main coronary artery 28'.

According to the embodiment of FIG. 6A and 6B, a catheter 90 is provided which consists of an elongated tubular member having a straight portion 92 (shown partially in FIG. 6A and 6B) and a distal end portion consisting of a first curved portion 94, a second curved portion 96 and a tip portion 98. The first curved portion 94 is concave (when viewed from the front as shown in FIG. 6B) having a radius of curvature of approximately 3 cm. and its second curved portion is convex having a radius of curvature of approximately 1 cm. The second curved portion 96 continues from the first curved portion 94 when the latter extends approximately 30–45 degrees from the vertical as shown in FIG. 6A. The length of the tip portion 98 is approximately 1 cm., and the tip portion 98 extends in the same direction as the straight portion 92, i.e. vertically as viewed in FIG. 6A. The lengths of the curves 94 and 96 are such that the outside wall of the tip portion 98 is spaced a distance D1 of approximately 2.5 cm. from the outside wall of the straight portion 92.

FIG. 6C depicts the cardiovascular system 22 with the catheter 90 inserted therein. The catheter 90 is a special application catheter designed to provide treatment for a venous bypass 100 which connects the aorta 24 to the distal segment of the right coronary artery 28. Due to the pre-shape of the catheter 90 shown in FIGS. 6A and 6B, the catheter, after insertion into the cardiovascular system 22 in the manner described above, it takes the position relative to the lumen of the venous bypass 100 shown in FIG. 6C. In this position the distal end of the tip portion 96, which forms the distal end of the catheter 90 is coaxially aligned with the lumen of the venous bypass 100.

According to an alternate embodiment of the catheter 90, the straight portion 92 can extend to an angle of approximately 10 degrees to 30 degrees to the vertical, as viewed and shown by the dashed line in FIG. 6A.

It is thus seen that the catheters embodied in the present invention are each specifically configured for more precise coaxial alignment with a particular artery in the cardiovascular system. Also, the catheters of the present invention provide improved support and guidance of associated catheters, such as balloon catheters, during angioplasty. Further, the catheters of the present invention form relatively small angles when inserted in the cardiovascular system, thus minimizing the dissipation of axial force during use.

It is understood that several variations may be made in the foregoing without departing from the scope of the invention. For example, the catheters embodied in the present invention are not limited for use as guiding catheters but can have other uses for treatment of the cardiovascular system, such as use as diagnostic, balloon, laser and atherectomy catheters, etc. Also, the specific lengths and angles of the specific examples of the catheters of the present invention set forth above can be varied within the scope of the invention. Moreover, it is understood that, instead of the well defined lengths and angles shown and described in the above examples, the bent distal end portion of the catheters of the present invention can form more smoother curves within the scope of the invention.

Other modifications, changes and substitutions are intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. A femoral approach angioplasty guide catheter adapted for selective catheterization of a left main coronary artery within a cardiovascular system comprising:
   an elongate flexible tubular member in a relaxed state prior to insertion in the cardiovascular system further comprising in consecutive arrangement:
   a first straight proximal portion extending distally from a proximal end of the tubular member;
   a second straight portion joined to the first straight portion and having a length of at least about 0.5 centimeters;
   a first curved portion defining a junction of the first straight portion and the second straight portion and defining a vertex of an obtuse angle of 130° to 150° between the first and second straight portion;
   a second curved portion joined to the second straight portion, said second portion having an apex and having an arcuate curvature of approximately 180° and a radius of curvature of about 1 centimeter;
   a third straight portion joined to the second curved portion;
   a fourth straight portion joined to the third straight portion and having a distal end defining a terminal distal tip of the tubular member; and
   a third curved portion defining a junction of the third straight portion and the fourth straight portion and defining a vertex of an obtuse angle of 13020 to 160° between the third straight portion and the fourth straight portion,
   wherein the interiors of the first curved portion and every curved portion distal thereof, including the second curved portion and the third curved portion, all generally face each other,
   wherein the first straight portion, second straight portion, third straight portion, and fourth straight portion all lie in generally the same plane, the third straight portion and the fourth straight portion extend slightly out of plane to the extend that the fourth straight overlaps the first straight portion, and
   wherein the distance between the apex of the second curved portion and the vertex of the third curved portion is about one-half the distance between the apex of the second curved portion and the terminal distal tip of the tubular member.

2. The catheter of claim 1 wherein, with the guide catheter configured so that when inserted in the cardiovascular system and the distal end of the fourth straight portion selectively engaged within an ostium of the left main coronary artery, the second straight portion rests against and substantially contiguous with a wall of the ascending aorta.

3. The catheter of claim 2 wherein the catheter is configured such that a proximal portion of the second curved portion rests against and substantially contiguous with the wall of the ascending aorta.

4. The catheter of claim 1 wherein the fourth straight portion is longer than the third straight portion.

5. A femoral approach angioplasty guide catheter adapted for selective catheterization of a left main coronary artery within a cardiovascular system comprising:
   an elongate flexible tubular member in a relaxed state prior to insertion in the cardiovascular system further comprising in consecutive arrangement:
   a first straight proximal portion extending distally from a proximal end of the tubular member;
   a second straight portion joined to the first straight portion and having a length of at least about 0.5 centimeters;
   a first curved portion defining a junction of the first straight portion and the second straight portion and defining a vertex of an obtuse angle of 130° to 150° between the first and second straight portions;
   a second curved portion joined to the second straight portion, said second portion having an apex and having an arcuate curvature of about 180° and a radius of curvature of about 1 centimeter;
   a third straight portion joined to the second curved portion and having a length of about 1 centimeter;
   a fourth straight portion joined to the third straight portion and having a length of about 2.3 to 3.1 centimeters, the fourth straight portion having a distal end defining a terminal distal tip of the tubular member; and
   a third curved portion defining a junction of the third straight portion and the fourth straight portion and defining a vertex of an obtuse angle of 130° to 160° between the third and fourth straight portions,
   wherein the interiors of the first curved portion and every curve portion distal thereof, including the second curved portion and the third curved portion, all generally face each other,
   wherein the first straight portion, second straight portion, third straight portion, and fourth straight portion all lie in generally the same plane, the third straight portion and the fourth straight portion extend slightly out of plane to the extent that the fourth straight portion overlaps the first straight portion, and
   wherein the distance between the apex of the second curvature portion and the vertex of the third curved portion is about one half the distance between the apex of the second curved portion and the terminal distal tip of the tubular member.

6. The catheter of claim 5 wherein the catheter is configured such that a proximal portion of the second curved portion and the second straight portion rest against and substantially contiguous with the wall of the ascending aorta.

* * * * *